(12) United States Patent
Aoyama

(10) Patent No.: US 6,827,963 B2
(45) Date of Patent: Dec. 7, 2004

(54) FATS AND OILS COMPOSITION FOR REDUCING LIPIDS IN BLOOD

(75) Inventor: Toshiaki Aoyama, Izumisano (JP)

(73) Assignee: The Nisshin OilliO, Ltd., Tokyo (JP)

(*) Notice: Subject to any disclaimer, the term of this patent is extended or adjusted under 35 U.S.C. 154(b) by 0 days.

(21) Appl. No.: 10/351,400

(22) Filed: Jan. 27, 2003

(65) Prior Publication Data
US 2003/0170368 A1 Sep. 11, 2003

Related U.S. Application Data

(63) Continuation-in-part of application No. 10/028,315, filed on Dec. 28, 2001.

(51) Int. Cl.$^7$ ............................................... A23D 9/00
(52) U.S. Cl. ........................ 426/606; 426/607; 554/227
(58) Field of Search .......................... 426/2, 601, 606, 426/607; 554/227

(56) References Cited

U.S. PATENT DOCUMENTS

| | | | | |
|---|---|---|---|---|
| 4,753,963 A | | 6/1988 | Jandacek et al. ............ 514/552 |
| 4,832,975 A | * | 5/1989 | Yang .......................... 426/607 |
| 5,000,975 A | * | 3/1991 | Tomarelli .................... 426/602 |
| 5,104,678 A | * | 4/1992 | Yang .......................... 426/601 |
| 5,142,071 A | * | 8/1992 | Kluesener et al. .......... 554/172 |
| 5,142,072 A | * | 8/1992 | Stipp et al. ................. 554/172 |
| 5,169,670 A | * | 12/1992 | Yang .......................... 426/607 |
| 5,360,336 A | * | 11/1994 | Monoe .......................... 432/5 |
| 5,681,606 A | * | 10/1997 | Hutchison et al. .......... 426/590 |
| 5,681,608 A | | 10/1997 | Cain et al. ................... 426/606 |
| 6,277,432 B1 | * | 8/2001 | Chang ........................ 426/602 |

FOREIGN PATENT DOCUMENTS

| | | |
|---|---|---|
| EP | 0 322 027 | 6/1989 |
| JP | 59-190948 | 10/1984 |
| JP | 63-087988 | 4/1988 |
| JP | 63-312398 | 12/1988 |
| JP | 01-186822 | 7/1989 |
| JP | 07-278010 | 10/1995 |
| JP | 08-269478 | 10/1996 |
| JP | 08-280358 | 10/1996 |
| JP | 09-013075 | 1/1997 |
| JP | 10-229841 | 9/1998 |
| JP | 2000-309794 | 11/2000 |
| JP | 2001-169753 | 6/2001 |
| JP | 2001-186845 | 7/2001 |
| JP | 2001-226693 | 8/2001 |
| JP | 2001-231491 | 8/2001 |
| JP | 2001-231492 | 8/2001 |
| WO | WO 89/02275 | 3/1989 |
| WO | WO 92/19237 | 11/1992 |
| WO | WO 94/24889 | 11/1994 |

OTHER PUBLICATIONS

US PgPub 2001/0005519.*
Lymphatic Absorption of Structured Glycerolipids Containing Medium–Chain Fatty Acids and Linoleic Acid, and Their Effect on Cholesterol Absorption in Rats, by Ikuo Ikeda, et al., *Lipids*, May 1991, vol. 26, No. 5, pp. 369–373.

* cited by examiner

*Primary Examiner*—Carolyn Paden
(74) *Attorney, Agent, or Firm*—Westerman, Hattori, Daniels & Adrian, LLP

(57) ABSTRACT

The present invention relates to fats and oils composition for reducing lipids in blood, comprising a triglyceride in which specified fatty acids are artificially combined at the first portion, the second portion and third portion of the triglyceride molecule. The present composition is preferably useful for foods. Such fats and oils composition for reducing lipids in blood, comprising triglycerides containing a $R_M R_L R_M$ triglyceride as an effective component, having Formula I. In formula I, wherein $R_M$ is an acyl group of a saturated medium chain fatty acid having 8 to 10 carbon atoms, $R_L$ is an acyl group of a monounsaturated long chain fatty acid having 16 to 18 carbon atoms, $C^1$ is the first carbon of the triglyceride, $C^2$ is the second carbon of the triglyceride, and $C^3$ is the third carbon of the triglyceride.

(Formula I)

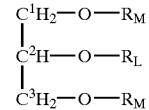

19 Claims, No Drawings

FATS AND OILS COMPOSITION FOR REDUCING LIPIDS IN BLOOD

CROSS-REFERENCE TO RELATED APPLICATIONS

This application is a continuation-in-part of application Ser. No. 10/028,315, filed Dec. 28, 2001.

BACKGROUND OF THE INVENTION

The present invention relates to a fats and oils composition for reducing lipids in blood, and in particular, the present invention relates to a fats and oils composition for reducing lipids in blood (blood fat), comprising a triglyceride as an effective compound in which specified fatty acids are combined at the first carbon, second carbon and third carbon of the triglyceride. The present composition is preferably useful for cooking or foods.

Recently and in particular in Japan, the number of persons who suffer from ischemic heart disease or brain infarction has increased, and the average of age of the persons who suffer from such diseases has been getting younger and younger. These diseases are generally caused by arteriosclerosis, which mainly results from deposition of cholesterol and otherwise lipids in the blood vessel. It is considered that hypercholesterolemia or hyperlipidemia is one of the dangerous factors that causes arteriosclerosis. Although Japanese people used to have a cholesterol value in plasma lower than that of Europeans or Americans, it is reported that recently, there is no significant difference in the cholesterol value in plasma, in particular between Japanese teenagers and European or American teenagers. It is considered to be due to the recent change in Japanese eating habit. Therefore, it has been said that it is required to take necessary and prompt measures related to diet in order to prevent arteriosclerosis from the period of childhood (Current internal Medicine 3, Hiperlipidemia edited by Haruo Nakamura, pages 44 to 52, published by Kanahara & Co., Ltd., 1995).

Several medicines for promoting lipid metabolisms are already commercially available, including HMG-CoA reductase inhibitors, linoleic acid derivative formulations, fibric acid formulations, nicomol formulations, unsaponified soybean oils, esterases, dextran sodium sulfate, artoron, probucol, and colestyramire. However, there is a report that these medicines may sometimes cause side effects such as kidney impairment, liver impairment, fever, and anaphylaxis, so as not to be said to be complete safety. Also, these medicines may not be applied to a person who is supersensitive to medicines, pregnant, or suffering from liver disease (A Book To Know A Medicine Prescribed By A Doctor written by Shigeru Kimura, pages 147 to 154, published by Hhoken Shuppan Co., Ltd., 2000).

Further, several formulations for lipid metabolisms that have improved in safety and effectiveness have been invented. See Japanese Laid Open Patent Publications Nos. 07-278010, 08-280358, 10-229841 and 2001-169753. However, such improved formulations have not become widespread, and in addition, are not easy to apply to our daily life. Recent National Nutrition Research reports that 59.6% of Japanese in their 40's suffer firm hyperlipidemia [The Present State of the Nutrition of the Nation edited by Kenko Eiyo Joho Kenkyukai (Health and Nutrition Information Research), "The Result of the National Nutrition Research in 1999", page 45, published by Dai-ichi Shuppan Publishing Co., Ltd., 2001]. Therefore, novel formulations for reducing lipids in blood, that not only provide safety and effectiveness but also is easily applied in our daily life, has been in demand.

On the other hand, several patents or patent applications have disclosed functionalities with respect to the structure of triglycerides. For example, Seto et al. discloses in Japanese Patent No. 1728708 that a structured fats and oils compound in which a fatty acid having 8 to 14 carbon atoms is combined at the second carbon of the triglyceride, and a fatty acid having 18 or more carbon atoms is combined at the first and the third carbons of the triglyceride, may be superior in digestion and absorption, the patent being assigned to Nisshin Oil Mills Ltd,. Also, Seto et al. discloses a structured fats and oils composition in Japanese Laid Open Patent Publication No. 9-13075, which is assigned to Nissin Oil Mills Ltd,. The structured fats and oils composition comprises a triglyceride, in which a n-3 long chain multivalent unsaturated fatty acid is combined, and less than 40 mole % of which is combined at the second carbon of the triglyceride, may have an improved property in lipid metabolisms in blood. Furthermore, Cain et al. discloses in U.S. Pat. No. 5,681,608 that triglycerides, in which an unsaturated fatty acid having 18 and more carbon atoms is combined at the second carbons of the triglycerides in an amount of 35 to 99.5%, may be superior in ingestion and absorption. However, there is no mention of fatty acids combined at the first and the third carbons of the triglycerides.

Thus, the present invention provides a novel fats and oils composition for reducing lipids in blood, which is superior not only in safety and effectiveness but also in easy application to our daily life. Also., the present invention provides novel foods containing such fats and oils composition for reducing lipids in blood.

DESCRIPTION OF THE INVENTION

The present inventor has investigated fats and oils compositions for the purpose of reducing lipids in blood, in the view of the above problems, and finally found that a triglyceride as an effective component, in which a selected fatty acid is combined at each of the first, second and third carbons of the triglyceride, may accomplish reduction of lipids in blood.

According to the present invention, there is provided a fats and oils composition for reducing lipids in blood, comprising triglycerides containing a $R_M R_L R_M$ triglyceride as an effective component. The $R_M R_L R_M$ triglyceride has Formula I as follows:

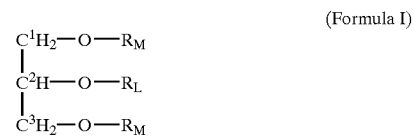

(Formula I)

According to the present invention, the triglycerides may further contain a $R_L R_L R_M$ triglyceride and/or a $R_M R_L R_L$ triglyceride.

The $R_L R_L R_M$ triglyceride has Formula II as follows:

(Formula II)

The $R_M R_L R_L$ triglyceride has Formula II' as follows:

(Formula II')

Also, according to the present invention, the triglycerides may further contain a $R_M R_M R_L$ triglyceride and/or a $R_L R_M R_M$ triglyceride.

The $R_M R_M R_L$ triglyceride has Formula III as follows:

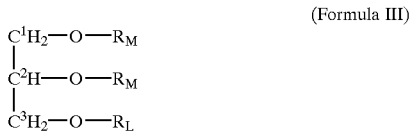

(Formula III)

Also, the $R_L R_M R_M$ triglyceride has Formula III' as follows:

(Formula III')

In the Formulas I, II, II', III and III', $R_M$ is an acyl group of a saturated medium chain fatty acid having 8 to 10 carbon atoms, $R_L$ is an acyl group of a monounsaturated long chain fatty acid having 16 to 18 carbon atoms, $C^1$ is the first carbon of the triglyceride, $C^2$ is the second carbon of the triglyceride, and $C^3$ is the third carbon of the triglyceride. In the Formulas above, two $R_M$s or $R_L$s are bonded in a molecule, which may be the same as or different from each other.

Also, according to the present invention, in the total mass of all the acyl groups in the triglycerides, $R_L$ (that is, the acyl group of a monounsaturated long chain fatty acid having 16 to 18 carbon atoms) may be contained in an amount of 60 to 90 mass %, and $R_M$ (that is, the acyl group of a saturated medium chain fatty acid having 8 to 10 carbon atoms) may be contained in an amount of 10 to 29 mass %. Also, in the total mass of the acyl groups of all the long chain fatty acids in the triglycerides, $R_L$ (that is, the acyl group of a monounsaturated long chain fatty acid having 16 to 18 carbon atoms) may be contained in an amount of 70 to 99 mass %. In addition, in the total mass of all the acyl groups combined at the portion of $C^2$ in the triglycerides, $R_L$ (that is, the acyl group of a monounsaturated long chain fatty acid having 16 to 18 carbon atoms) may be contained in an amount of 70 to 99 mass %.

Also, according to the present invention, $R_M$ may be acyl group of caprylic acid, and $R_L$ may be acyl group of oleic acid.

Also, according to the present invention, in the fats and oils composition for reducing lipids in blood, the $R_M R_L R_M$ triglyceride may be contained in an amount of 5 to 25 mass %.

Also, according to the present invention, in the fats and oils composition for reducing lipids in blood, the $R_L R_L R_M$ triglyceride and/or the $R_M R_L R_L$ triglyceride may be contained in an amount of 45 to 65 mass %.

Further, the fats and oils composition for reducing lipids in blood may be applied to foods. Such foods may include cooking oil, mayonnaise, mayonnaise fake foods, margarine, dressing, bread, ice cream, confectionary, gelatine capsule and fried foods.

Instead of the $R_M R_L R_M$ triglyceride having Formula I contained as an effective component of the fats and oils composition for reducing lipids in blood, the $R_L R_L R_M$ triglyceride having Formula II and/or the $R_M R_L R_L$ triglyceride having Formula II' as described before may be contained in the composition as an effective component. In such case, the $R_M R_L R_M$ triglyceride having Formula I may be further contained in the present composition. Additionally, the $R_M R_M R_L$ triglyceride having Formula III and/or the $R_L R_M R_M$ triglyceride having Formula III' may be contained in the present composition.

On the other hand, instead of the $R_M R_L R_M$ triglyceride having Formula I contained as an effective component of the fats and oils composition for reducing lipids in blood as described before, the $R_M R_M R_L$ triglyceride having Formula III and/or the $R_L R_M R_M$ triglyceride having Formula III' may be contained in the composition as an effective component. In such case, the $R_M R_L R_M$ triglyceride having Formula I may be further contained in the present composition. Additionally, the $R_L R_L R_M$ triglyceride having Formula II and/or the $R_M R_L R_L$ triglyceride having Formula II' may be contained in the present composition.

DETAILED DESCRIPTION OF THE INVENTION

According to the present invention, the lipids in blood may include total cholesterol, LDL cholesterol and neutral fat in blood. Generally speaking, the lipids in blood may be measured by analyzing plasma or serum.

According to the present invention, one of effective components in the fats and oils composition for reducing lipids in blood is a $R_M R_L R_M$ triglyceride in which a saturated medium chain fatty acid having 8 to 10 carbon atoms is combined at the first and the third carbons of the triglyceride, and a monounsaturated long chain fatty acid having 16 to 18 carbon atoms is combined at the second carbon of the triglyceride.

The monounsaturated long chain fatty acid having 16 to 18 carbon atoms may include, but is not to be limited to, palmitoleic acid, oleic acid, petroselinic acid, elaidic acid, and vaccenic acid. Monounsaturated fatty acids whose double bond is located at a different portion from, and in relation of isomer to, those listed above, may be included in the monounsaturated long chain fatty acid. Also, acids in relation to cis or trans isomerism of those listed above may be included in the monounsaturated long chain fatty acid. Further, monounsaturated hydroxy acids such as ricinoleic acid and densipolic acid, and monounsaturated epoxy acids such as vernolic acid, as well as monounsaturated keto acids may be included in the monounsaturated long chain fatty acid. In particular, oleic acid may be preferable as the monounsaturated long chain fatty acid having 16 to 18 carbon atoms according to the present invention.

The saturated medium chain fatty acid having 8 to 10 carbon atoms may include, but is not to be limited to, caprylic acid, capric acid, saturated monohydroxy acids, saturated polyhydroxy acids, and polyyne acid. In particular, caprylic acid may be preferable as the saturated medium chain fatty acid having 8 to 10 carbon atoms according to the present invention.

The $R_M R_L R_M$ triglyceride of the effective component may be contained in the fats and oils composition according to the present invention in an amount of 0.1 to 99.9 mass %, but in particular, preferably in an amount of 3 to 80 mass %, and more preferably in an amount of 3 to 50 mass %, and most preferably in an amount of 5 to 25 mass %, and especially in an amount of 10 to 20 mass %. When a person eats foods containing the composition including the $R_M R_L R_M$ triglyceride in the amount mentioned above, his or her lipids in bloods are expected to reduce.

In addition to the $R_M R_L R_M$ triglyceride, the fats and oils composition according to the present invention may contain a $R_L R_L R_M$ triglyceride represented by Formula II and/or a $R_M R_L R_L$ triglyceride represented by Formula II'. The $R_L R_L R_M$ triglyceride and/or the $R_M R_L R_L$ triglyceride may be contained preferably in an amount of 45 to 65 mass %, and more preferably in an amount of 50 to 60 mass %, in the composition according to the present invention.

Further, the fats and oils composition according to the present invention may contain a $R_M R_M R_L$ triglyceride represented by Formula III and/or a $R_L R_M R_M$ triglyceride represented by Formula III'.

Also, in case of further containing the $R_L R_L R_L$ triglyceride, the $R_L R_L R_L$ triglyceride may be contained preferably in an amount of 25 to 45 mass %, and more preferably in an amount of 30 to 40 mass %, and more preferably in an amount of 50 to 60 mass %, in the composition according to the present invention.

These amounts of the triglycerides may improve in application to cooking or foods.

In the total mass of all the acyl groups in the triglycerides, $R_L$ (that is, the acyl group of a monounsaturated long chain fatty acid having 16 to 18 carbon atoms), which is preferably the acyl group of oleic acid, is contained preferably in an amount of 60 to 90 mass %, and more preferably in an amount of 70 to 80 mass %. In such an amount of $R_L$ (that is, the acyl group of a monounsaturated long chain fatty acid having 16 to 18 carbon atoms), the composition according to the present invention may improve reduction of lipids in blood.

In the total mass of all the acyl groups in the triglycerides, $R_M$ (that is, the acyl group of a saturated medium chain fatty acid having 8 to 10 carbon atoms), which is preferably the acyl group of caprylic acid, is contained preferably in an amount of 10 to 29 mass %, and more preferably in an amount of 15 to 25 mass %. In such an amount of $R_M$ (that is, the acyl group of a saturated medium chain fatty acid having 8 to 10 carbon atoms), applicability to cooking or foods may be improved.

In the total mass of the acyl groups of all the long chain fatty acids in the triglycerides, $R_L$ (that is, the acyl group of a monounsaturated long chain fatty acid having 16 to 18 carbon atoms), which is preferably the acyl group of oleic acid, may be contained preferably in an amount of 70 to 99 mass %, and more preferably in an amount of 75 to 95 mass %. The present composition may be further improved to reduce lipids in blood. According to the present invention, the long carbon chain fatty acid means a fatty acid having 14 or more carbon atoms, including the monounsaturated long chain fatty acid having 16 to 18 carbon atoms.

In the total mass of all the acyl groups combined at the portions of $C_2$ in the triglycerides, $R_L$, which is preferably the acyl group of oleic acid, may be contained preferably in an amount of 70 to 99 mass %, and more preferably in an amount of 80 to 95 mass %. When such an amount of $R_L$ is combined at the second carbons of the triglycerides, the composition may have a significant effect of reducing lipids in blood.

In addition, according to the present invention, the triglycerides may further contain a $R_L R_L R_L$ triglyceride. The $R_L R_L R_L$ triglyceride has Formula IV as follows:

Also, according to the present invention, the triglycerides may further contain a $R_M R_M R_M$ triglyceride. The $R_M R_M R_M$ triglyceride has Formula V as follows:

Also, according to the present invention, the triglycerides may further contain a $R_L R_M R_L$ triglyceride. The $R_L R_M R_L$ triglyceride has Formula VI as follows:

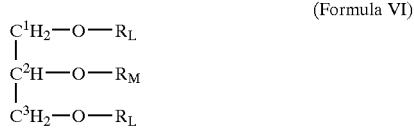

In Formulas IV, V and VI, $R_M$ is an acyl group of a saturated medium chain fatty acid having 8 to 10 carbon atoms, $R_L$ is an acyl group of a monounsaturated long chain fatty acid having 16 to 18 carbon atoms, $C^1$ is the first carbon of the triglyceride, $C^2$ is the second carbon of the triglyceride, and $C^3$ is the third carbon of the triglyceride.

One of the preferable fats and oils compositions of the present invention may have a constitution as follows, but is not to be limited thereto.

A fats and oils composition for reducing lipids in blood comprising triglycerides containing:

an $R_M R_L R_M$ triglyceride having Formula I, wherein $R_M$ is acyl group of caprylic acid, and $R_L$ is acyl group of oleic acid, in an amount of 10 to 20 mass %, an $R_L R_L R_M$ triglyceride having Formula II and/or a $R_M R_L R_L$ triglyceride having Formula II', wherein $R_M$ is acyl group of caprylic acid and $R_L$ is acyl group of oleic acid, in an amount of 49 to 59 mass %, and an $R_L R_L R_L$ triglyceride having Formula IV, wherein $R_L$ is acyl group of oleic acid, in an amount of 30 to 40 mass %, wherein in the total mass of the acyl groups in the triglycerides, the acyl group of oleic acid is contained in an amount of 60 to 90 mass %, and the acyl group of caprylic acid is contained in an amount of 10 to 29 mass %, wherein in the total mass of the acyl groups of all the long carbon chain fatty acids in the triglycerides, the acyl group of oleic acid is contained in an amount of 70 to 99 mass %, and wherein in the total mass of all the acyl groups combined at the portions of the second carbon in the triglycerides, the acyl group of oleic acid is contained in an amount of 70 to 99 mass %.

According to the present invention, the fats and oils composition may include the other ingredients set forth above. For example, the fats and oils composition may include diacylglycerols (diglycerides). Such diacylglycerols may be included in the present composition preferably in an amount of less than 9.9 mass %, and more preferably in an amount of less than 4.9 mass %, and most preferably in an amount of less than 2.9 mass %. With such amount of the diacylglycerols, the composition according to the present invention may be useful for cooking or foods.

The fats and oils composition for reducing lipids in blood according to the present invention may taste as good as a commercially available cooking oils such as rapeseed oil, corn oil, safflower oil and soybean oil. Therefore, the fats and oils composition for reducing lipids in blood according to the present invention may not only be used for cooking such as fried foods, panned foods, marinades, but also be applied to processed foods.

By using the fats and oils composition for reducing lipids in blood according to the present invention, various foods may be cooked or applicable to other foods, while making the best use of the taste and flavor of the raw food material.

Also, when frying with using the present composition, the extent of splashing or bubbling of the present oil is as low as commercially available cooking oils.

If necessary, additives may be added to the fats and oils composition for reducing lipids in blood according to the present invention. Such additives may include polyglycerol fatty acid ester, saccharose fatty acid ester, sorbitan fatty acid ester, vitamin E, ascorbic acid fatty acid ester, lignan, coenzyme A, phosphorus lipids, oryzanol and diglycerides for the purpose of improving preservation stability, oxidation stability, heat stability and prevention of crystallization at low temperature. Also, such additives may include vitamin E, ascorbic acid fatty acid ester, lignan, coenzyme A, phosphorus lipids and oryzanol for the purpose of improving preventions of geriatric diseases, fatness and biooxidation. Also, the fats and oils composition for reducing lipids in blood according to the present invention may be mixed with cooking oils such as soybean oil, rapeseed oil, rapeseed oil rich in oleic acid, corn oil, sesame seed oil, sesame salad oil, perilla oil, linseed oil, peanut oil, safflower oil, safflower oil rich in oleic acid, sunflower oil, sunflower oil rich in oleic acid, cotton seed oil, grape seed oil, macadamia nut oil, hazelnut oil, pumpkin seed oil, walnut oil, camellia oil, tea seed oil, egoma oil, perilla oil, borage oil, olive oil, rice bran oil, wheat embryo oil, seal oil and algae oil, and above listed oils improved by being poor-saturated, hydrogenerated or segregated.

Relating to intake of the fats and oils composition for reducing lipids in blood according to the present invention, the triglyceride as an effective component may be taken preferably in an amount of 1 to 60 grams, and more preferably in an amount of 2 to 30 grams, and most preferably in an amount of 5 to 20 grams, daily. Furthermore, the triglyceride as an effective component may be taken preferably in an amount of 0.5 to 30 grams, and more preferably in an amount of 1 to 20 grams, and most preferably in an amount of 5 to 16 grams, at every meal.

The fats and oils composition for reducing lipids in blood according to the present invention may be applied to cooking oils, mayonnaise, mayonnaise fake foods (that are, foods in imitation of mayonnaise), margarine, dressing, bread, ice cream, confectionary, gelatine capsule and fried foods, for the purpose of easily applying the fats and oils composition to our daily meals and reducing lipids in blood.

Furthermore, in such foods, the fats and oils composition for reducing lipids in blood according to the present invention may be preferably contained in such amount that the triglyceride as an effective component is contained in an amount of 0.1 to 99 mass %, and more preferably in an amount of 1 to 80 mass %, and most preferably in an amount of 10 to 77 mass %.

Also, these foods may contain food additives such as emulsifying agents, antioxidation agents, coloring agents, flavor agents and preservatives, which are well known to the persons of ordinary skills in the art.

Also, such foods may be prepared, produced or cooked, but are not to be limited thereto, in well known manner.

The fats and oils composition for reducing lipids in blood according to the present invention may be prepared by means of, but not to be limited to, an enzyme method, a chemical synthesis method, a method of extracting from natural fats and oils, and a genetic recombination method of oil seeds. In the case where the fats and oils composition for reducing lipids in blood according to the present invention is prepared by means of an enzyme method, a triglyceride of monounsaturated long chain fatty acid may react with a saturated medium chain fatty acid having 8 to 10 carbon atoms in the presence of an enzyme. The triglyceride used for such reaction may be selected from, but is not to be limited to, synthesized and natural oils such as soybean oil, rapeseed oil, rapeseed oil rich in oleic acid, corn oil, sesame seed oil, sesame salad oil, perilla oil, linseed oil, peanut oil, safflower oil, safflower oil rich in oleic acid, sunflower oil, and sunflower oil rich in oleic acid.

The enzyme used for preparing the fats and oils composition according to the present invention may be any one which selectively makes reaction at the first and the third portions of the triglyceride. The enzyme may include lipase, esterase and so on. The enzyme may be in an immobilized state or in powder state, but is not to be limited thereto. After the reaction, free fatty acids may be removed by means of distillation, absorption, alkalization removal and so on, but are not to be limited thereto. Thereafter, purification may be conducted if necessary. Such purification may be conducted by means of deoxidation treatment, decolonization treatment, deodorization treatment and so on, but is not to be limited thereto.

Embodiments

The following embodiments are recognized by the inventor as best modes, and useful for understanding the present invention, but shall not limit the scope of the present invention defined by the claims.

EXAMPLE 1

50 kg of tricaprylin, 50 kg of oleic acid and 5 kg of Lypozym IM60 (manufactured by Novo Co., Ltd.) were mixed together and reacted under heating at 50° C. for 20 hours. After the reaction, free fatty acids were removed by distillation. Thereafter, molecular distillation was conducted so as to obtain 1 kg of fraction of fats and oils composition (1), being rich in a triglyceride in which caprylic acids were combined at the first and second carbons thereof, or the second and third carbons thereof, which is hereinafter referred to as "8.8.O" or "O.8.8". Table 1 shows analyzed ingredients of composition (1).

EXAMPLE 2

40 kg of sunflower rich in oleic acid, 60 kg of caprylic acid and 5 log of Lypozym 1M 60 (manufactured by NovoCo., Ltd.) were mixed together and reacted under heating at 50° C. for 20 hours. After the reaction, free fatty acids were removed by distillation. Thereafter, molecule distillation was conducted so as to obtain 1 kg of fraction of fats and oils composition (2), being rich in a triglyceride in which oleic acid was combined at the second carbon thereof and caprylic acids were combined at the first and third carbons thereof, which is hereinafter referred to as "8.O.8". Table 1 shows analyzed ingredients of composition (2).

TABLE 1

| Ingredients of the Triglyceride | Composition 1 | Composition 2 |
|---|---|---|
| "8.8.8" | 4.6 | 2.4 |
| "8.O.8" | — | 38.4 |
| "O.8.8" or "8.8.O" | 84.7 | 31.4 |
| "8.L.8" | — | 2.9 |
| "8.8.L" or "L.8.8" | — | 2.4 |
| "8.O.O" or "O.O.8" | 4.7 | 10.7 |
| "8.L.L" or "L.L.8" | — | 0.9 |
| Others | 6.0 | 10.9 |

In Table 1, "8" represents caprylic acid, "O" represents oleic acid, and "L" represents a long chain fatty acid other than oleic acid. For example, in "8.L.8," the left symbol "8" shows caprylic acid that is a fatty acid combined at the 1st carbon of the triglyceride, and the middle symbol "L" shows a long chain fatty acid except oleic acid that is a fatty acid combined at the 2nd carbon of the triglyceride, and the right symbol "8" shows caprylic acid that is a fatty acid combined at the 3rd carbon of the triglyceride. In other wards, "8.L.8" represents a triglyceride in which a long chain fatty acid other than oleic acid is combined at the second carbon thereof and caprylic acids are combined at each of the first and the third carbons thereof.

Tests of the Effect of the Fats and Oils Composition

Eighteen F1B hamsters were purchased for this test. Commercial solid diet were fed to them for one week and they were adapted to their new circumstances. Then, all of the hamsters were fed a commercially available feed containing 10 mass % of coconut oil and 0.1 mass % of cholesterol, that is a higher cholesterol feed, for two weeks. After the period of such feeding, they were not fed for one night before blood was taken from their eyegrounds for measuring a concentration of LDL cholesterol. Then, the hamsters were divided into three groups, (1), (2) and (3), each group having six hamsters with having a similar average in their LDL-cholesterol and weight. Each group of the hamsters was fed feeds shown in Table 2 for two weeks. After the period of such feeding, they were not fed for one night before blood was taken from their eyegrounds. The blood was centrifuged in order to obtain plasma. The concentrations of total cholesterol, LDL-cholesterol, HDL-cholesterol and triglycerides in the plasma were measured. Table 3 shows the results.

The group rich in "O.8.8" has a lower average of the concentration of total cholesterol than that of the group of control. The group rich in "8.O.8" has a much lower average of the concentration of total cholesterol than that of the group of control.

The group rich in "O.8.8" has a lower average of the concentration of LDL-cholesterol than that of the group of control. The group rich in "8.O.8" has a much lower average of the concentration of LDL-cholesterol then that of the group of control.

The group rich in "O.8.8" has a slight lower average of the concentration of HDL-cholesterol than that of the group of control. The group rich in "8.O.8" has a lower average of the concentration of HDL-cholesterol than that of the group of control.

The group rich in "O.8.8" has a slight lower average of the concentration of neutral fat than that of the group of control. The group rich in "8.O.8" has approximately 100 mg/dl lower average of the concentration of neutral fat than that of the group of control.

TABLE 2

| Groups | fed meal |
|---|---|
| group of control | meal containing 10 mass % of coconut oil and 0.1 mass % of cholesterol |
| group rich in "O.8.8" | meal containing 10 mass % of composition (1) and 0.1 mass % of cholesterol |
| group rich in "8.O.8" | meal containing 10 mass % of composition (2) and 0.1 mass % of cholesterol |

TABLE 3

(mg/dl)

| | group of control | Group rich in "O.8.8" | group rich in "8.O.8" |
|---|---|---|---|
| Concentration of Total Cholesterol | 443 ± 47 | 264 ± 13[1)] | 226 ± 8[1)2)] |
| Concentration of LDL-Cholesterol | 305 ± 20 | 163 ± 11[1)] | 130 ± 8[1)2)] |
| Concentration of HDL-cholesterol | 138 ± 30 | 101 ± 5 | 95 ± 4 |
| Concentration of Neutral Fat | 291 ± 46 | 285 ± 41 | 193 ± 22 |

The concentrations in the table shows averages and standard errors.
[1)]There was found a significant difference compared with the control group. (The level of significance was 5% or less.)
[2)]There was found a significant difference compared with the group rich in "O.8.8." (The level of significance was 5% or less.)

EXAMPLE 3

(Preparation of Fats and Oils)

40 kg of trioleilin, 60 kg of caplyric acid and 5 kg of Lypozym 1M60 (manufactured by Novo Co., Ltd.) were mixed together and reacted under heating at 50° C. for 20 hours. After the reaction, free fatty acids were removed by distillation. Thereafter, molecular distillation was conducted so as to obtain 1 kg of fraction of fats and oils composition 3, containing "8.O.8" triglyceride. Table 4 shows analyzed ingredients of composition 3.

TABLE 4

(g/100 g)

| Molecule contained in the triglycerides | Fats and oils composition 3 |
|---|---|
| 8.8.8 | 1.0 |
| 8.O.8 | 16.1 |
| 8.O.O (or O.O.8) | 43.1 |
| Others | 27.0 |

In the table, "8" represents caprylic acid, and "O" represents oleic acid. For example, in "8.O.8," the left symbol "8" Shows caprylic acid that is a fatty acid combined at the 1st carbon of the triglyceride, and the middle symbol "O" shows oleic acid that is a fatty acid combined at the 2nd carbon of the triglyceride, and the right symbol "8" shows caprylic acid that is a fatty acid combined at the 3rd carbon of the triglyceride. In other wards, "8.O.8" represents a triglyceride in which oleic acid is combined at the second carbon thereof and caprylic acids are combined at each of the first and the third carbons thereof.

EXAMPLE 4
Tests of the Effect of the Fats and Oils Composition

Ten F1B hamsters were purchased for this test. Commercial solid diet were fed to them for one week and they were adapted to their new circumstances. Then, all of the hamsters were fed a commercially available feed containing 10 mass % of coconut 1 and 0.1 mass % of cholesterol, that is a higher cholesterol feed, for two weeks. After the period of such feeding, they were not fed for one night before blood was taken from their eyegrounds for measuring a concentration of LDL cholesterol. Then, the hamsters were divided into three groups, (1), (2) and (3), each group having five hamsters with having a similar average in their LDL-cholesterol and weight. Each group of the hamsters was fed feeds shown in Table 5 for two weeks.

TABLE 5

| Groups | Fed meal |
| --- | --- |
| Group of control | meal containing 10 mass % of coconut oil |
| group of composition 3 contained | meal containing 10 mass % of composition 3 |

After the period of such feeding, they were not fed for one night before blood was taken from their eyegrounds. The blood was centrifuged in order to obtain plasma. The concentrations of total cholesterol and neutral fat were measured. Table 6 shows the results.

The group of the composition 3 contained has a significant lower average of the concentration of total cholesterol than that of the group of control. The group of the composition 3 contained has a lower average of the concentration of neutral fat than that of the group of control. There is found that even if "8.O.8" triglyceride is contained in an amount as low as 16 mass % in the triglycerides, it affects on reducing lipids in blood.

TABLE 6

| | (mg/dl) | |
| --- | --- | --- |
| | group of control | group of composition 3 contained |
| Concentration of Total Cholesterol | 267 ± 7 | 231 ± 8[1)] |
| Concentration of neutral fat | 260 ± 29 | 232 ± 30 |

The concentrations in the table shows averages and standard errors.
[1)]There was found a significant difference compared with the control group. (The level of significance was 5% or less.)

What is claimed is:

1. A fats and oils composition for reducing lipids in blood comprising triglycerides containing:
   an $R_M R_L R_M$ triglyceride as an effective component, having Formula I:

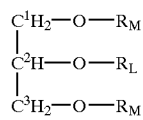

(Formula I)

wherein $R_M$ is acyl group of a saturated medium chain fatty acid having 8 to 10 carbon atoms, and $R_L$ is acyl group of a monounsaturated long chain fatty acid having 16 to 18 carbon atoms, and the $R_M R_L R_M$ triglyceride is contained in an amount of 5 to 25 mass %;

an $R_L R_L R_M$ triglyceride having Formula II and/or an $R_M R_L R_L$ triglyceride having Formula II':

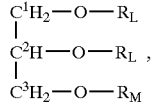

(Formula II)

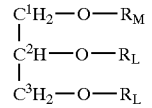

(Formula II')

wherein $R_M$ is acyl group of a saturated medium chain fatty acid having 8 to 10 carbon atoms and $R_L$ is acyl group of a monounsaturated long chain fatty acid having 16 to 18 carbon atoms, and the total amount of the $R_L R_L R_M$ and $R_M R_L R_L$ triglycerides is 45–65 mass %; and an $R_L R_L R_L$ triglyceride having Formula IV:

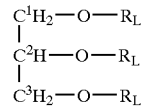

(Formula IV)

wherein $R_L$ is acyl group of a monounsaturated long chain fatty acid having 16 to 18 carbon atoms, the $R_L R_L R_L$ triglyceride is contained in an amount of 25 to 45 mass %.

2. A fats and oils composition for reducing lipids in blood according to claim 1, wherein in the formulas, $R_M$ is acyl group of caprylic acid and $R_L$ is acyl group of oleic acid.

3. A fats and oils composition for reducing lipids in blood according to claim 2, wherein the $R_M R_L R_M$ triglyceride is contained in an amount of 10 to 20 mass %.

4. A fats and oils composition for reducing lipids in blood according to claim 3, wherein the $R_L R_L R_L$ triglyceride is contained in an amount of 30 to 40 mass %.

5. A fats and oils composition for reducing lipids in blood according to claim 2, wherein the total amount of the $R_L R_L R_M$ and $R_M R_L R_L$ triglycerides is 50 to 60 mass %.

6. A fats and oils composition for reducing lipids in blood according to claim 5, wherein the $R_L R_L R_L$ triglyceride is contained in an amount of 30 to 40 mass %.

7. A fats and oils composition for reducing lipids in blood according to claim 2, wherein the $R_L R_L R_L$ triglyceride is contained in an amount of 30 to 40 mass %.

8. A fats and oils composition for reducing lipids in blood according to claim 2, wherein in the total mass of the acyl groups in the triglycerides, the acyl group of oleic acid is contained in an amount of 60 to 90 mass %, and the acyl group of caprylic acid is contained in an amount of 10 to 29 mass %, wherein in the total mass of the acyl groups of all the long carbon chain fatty acids in the triglycerides, the acyl group of oleic acid is contained in an amount of 70 to 99 mass %, and wherein in the total mass of all the acyl groups combined at the portions of the second carbon in the triglycerides, the acyl group of oleic acid is contained in an amount of 70 to 99 mass %.

9. A fats and oils composition for reducing lipids in blood according to claim 1, wherein the $R_M R_L R_M$ triglyceride is contained in an amount of 10 to 20 mass %.

10. A fats and oils composition for reducing lipids in blood according to claim 9, wherein the total amount of the $R_L R_L R_M$ and $R_M R_L R_L$ triglycerides is 50 to 60 mass %.

11. A fats and oils composition for reducing lipids in blood according to claim 10, wherein the $R_LR_LR_L$ triglyceride is contained in an amount of 30 to 40 mass %.

12. A fats and oils composition for reducing lipids in blood according to claim 9, wherein the $R_LR_LR_L$ triglyceride is contained in an amount of 30 to 40 mass %.

13. A fats and oils composition for reducing lipids in blood according to claim 9, wherein in the total mass of the acyl groups in the triglycerides, the acyl group of oleic acid is contained in an amount of 60 to 90 mass %, and the acyl group of caprylic acid is contained in an amount of 10 to 29 mass %, wherein in the total mass of the acyl groups of all the long carbon chain fatty acids in the triglycerides, the acyl group of oleic acid is contained in an amount of 70 to 99 mass %, and wherein in the total mass of all the acyl groups combined at the portions of the second carbon in the triglycerides, the acyl group of oleic acid is contained in an amount of 70 to 99 mass %.

14. A fats and oils composition for reducing lipids in blood according to claim 1, wherein the total amount of the $R_LR_LR_M$ and $R_MR_LR_L$ triglycerides is 50 to 60 mass %.

15. A fats and oils composition for reducing lipids in blood according to claim 14, wherein the $R_LR_LR_L$ triglyceride is contained in an amount of 30 to 40 mass %.

16. A fats and oils composition for reducing lipids in blood according to claim 14, wherein in the total mass of the acyl groups in the triglycerides, the acyl group of oleic acid is contained in an amount of 60 to 90 mass %, and the acyl group of caprylic acid is contained in an amount of 10 to 29 mass %, wherein in the total mass of the acyl groups of all the long carbon chain fatty acids in the triglycerides, the acyl group of oleic acid is contained in an amount of 70 to 99 mass %, and wherein in the total mass of all the acyl groups combined at the portions of the second carbon in the triglycerides, the acyl group of oleic acid is contained in an amount of 70 to 99 mass %.

17. A fats and oils composition for reducing lipids in blood according to claim 1, wherein the $R_LR_LR_L$ triglyceride is contained in an amount of 30 to 40 mass %.

18. A fats and oils composition for reducing lipids in blood according to claim 17, wherein in the total mass of the acyl groups in the triglycerides, the acyl group of oleic acid is contained in an amount of 60 to 90 mass %, and the acyl group of caprylic acid is contained in an amount of 10 to 29 mass %, wherein in the total mass of the acyl groups of all the long carbon chain fatty acids in the triglycerides, the acyl group of oleic acid is contained in an amount of 70 to 99 mass %, and wherein in the total mass of all the acyl groups combined at the portions of the second carbon in the triglycerides, the acyl group of oleic acid is contained in an amount of 70 to 99 mass %.

19. A fats and oils composition for reducing lipids in blood according to claim 1, wherein in the total mass of the acyl groups in the triglycerides, the acyl group of oleic acid is contained in an amount of 60 to 90 mass %, and the acyl group of caprylic acid is contained in an amount of 10 to 29 mass %, wherein in the total mass of the acyl groups of all the long carbon chain fatty acids in the triglycerides, the acyl group of oleic acid is contained in an amount of 70 to 99 mass %, and wherein in the total mass of all the acyl groups combined at the portions of the second carbon in the triglycerides, the acyl group of oleic acid is contained in an amount of 70 to 99 mass %.

\* \* \* \* \*